United States Patent [19]
Iida

[11] Patent Number: 5,662,588
[45] Date of Patent: Sep. 2, 1997

[54] ENDOSCOPE APPARATUS

[75] Inventor: Yoshihiro Iida, Hachioji, Japan

[73] Assignee: Olympus Optical Co., Ltd., Tokyo, Japan

[21] Appl. No.: 429,234

[22] Filed: Apr. 25, 1995

[30] Foreign Application Priority Data

May 31, 1994 [JP] Japan .................. 6-118153

[51] Int. Cl.$^6$ ...................................... A61B 1/04
[52] U.S. Cl. .................. 600/121; 600/124; 600/125; 600/127
[58] Field of Search .................. 600/121, 123, 600/124, 125, 127, 153, 156, 104, 106, 107

[56] References Cited

U.S. PATENT DOCUMENTS

| 4,646,722 | 3/1987 | Silverstein et al. ............... 600/121 X |
| 5,239,935 | 8/1993 | Takahashi ........................ 600/121 |

FOREIGN PATENT DOCUMENTS

| 51-103891 | 8/1976 | Japan . |
| 64-6804 | 2/1989 | Japan ................................. 600/121 |
| 2-54734 | 11/1990 | Japan . |
| 4-314439 | 11/1992 | Japan . |

*Primary Examiner*—Beverly M. Flanagan
*Attorney, Agent, or Firm*—Frishauf, Holtz, Goodman, Langer & Chick

[57] ABSTRACT

An endoscope apparatus including an insertion portion to be inserted into a body cavity, and a tip structure constituting a tip portion of the insertion portion. A tip cover is detachably mounted on the tip structure from a side of a tip portion of the tip structure such that the tip cover covers the tip structure. An engagement mechanism is provided on the insertion portion for detachably engaging the tip cover, and a hard finger driven engaging/disengaging member is provided on an outer periphery of a portion of the insertion portion which is located in the vicinity of the engagement mechanism.

20 Claims, 6 Drawing Sheets

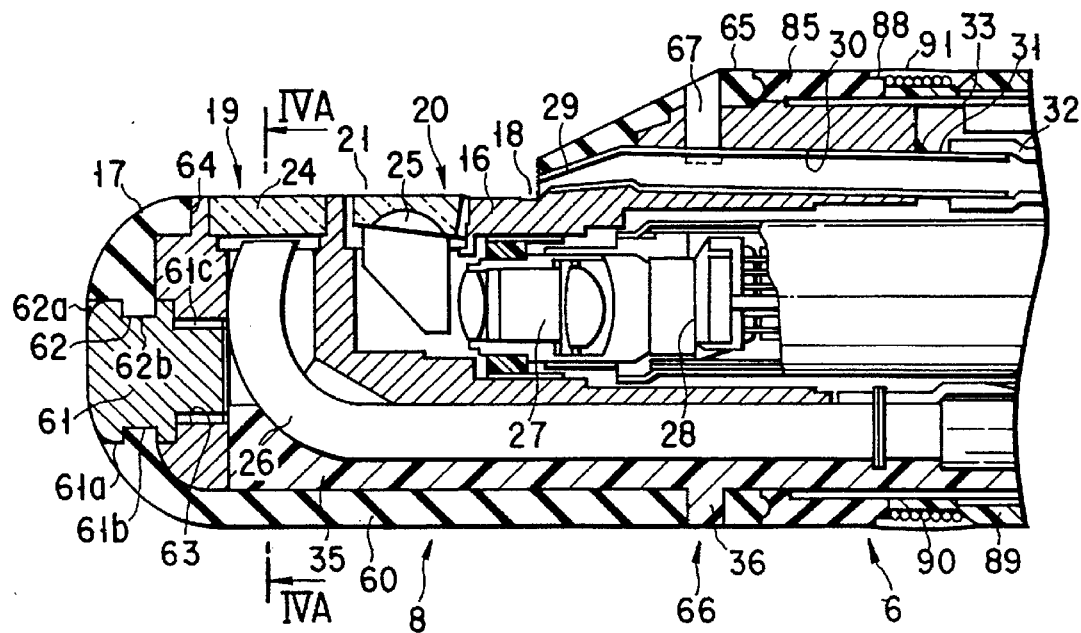
F I G. 1
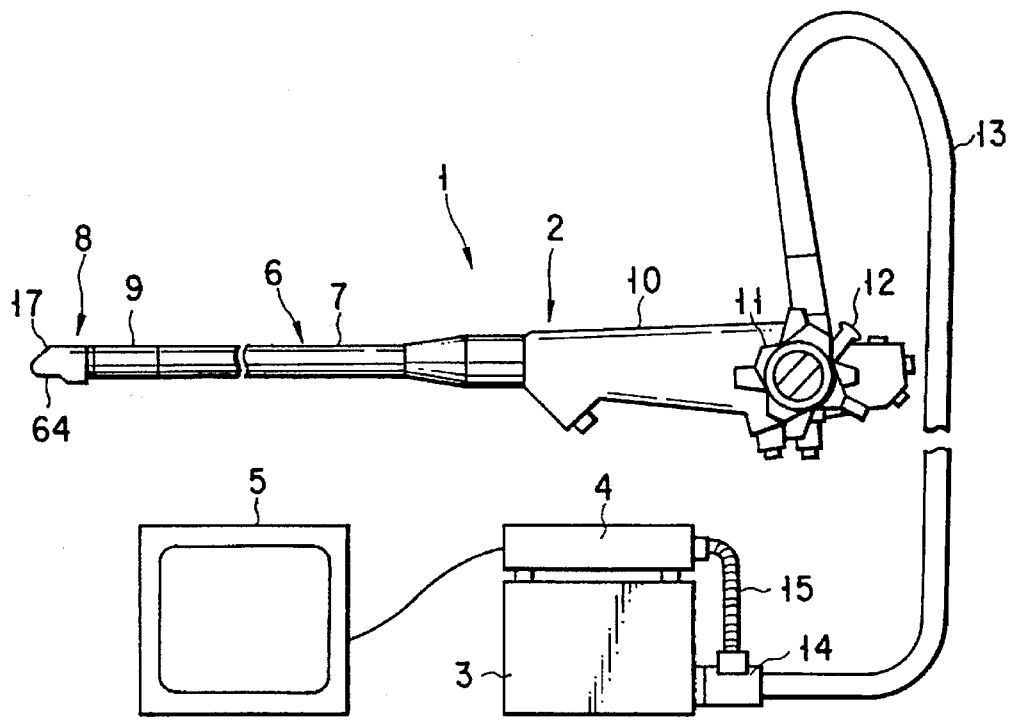
F I G. 2

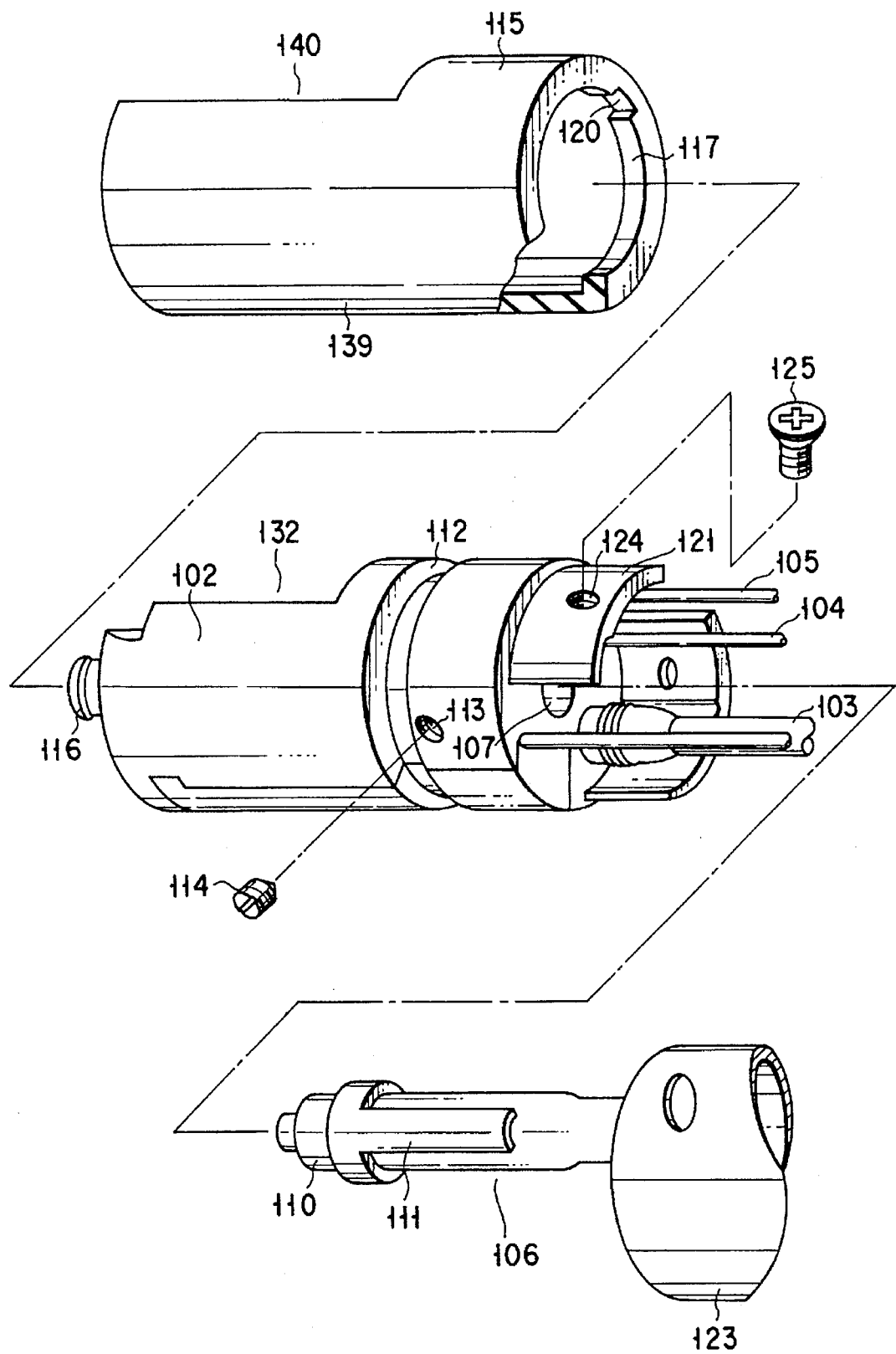
F I G. 8

1

ENDOSCOPE APPARATUS

BACKGROUND OF THE INVENTION

1. Field of the Invention

This invention relates to an endoscope apparatus having a tip cover detachably mounted on a tip portion of an insertion portion thereof to be inserted into a body cavity (including a corporeal tube).

2. Description of the Related Art

In general, a side-view endoscope of a tip-cover detachable type is known, for example, from Jpn. Pat. Appln. KOKAI Publication No. 4-314439, in which a tip cover is detachably mounted on a tip portion of an insertion portion to be inserted into a body cavity. The tip cover of an endoscope of this type is made of a relatively hard material.

Further, Jpn. UM Appln. KOKAI Publication No. 51-103891 discloses an elastic cover which covers the entire insertion portion of an endoscope. Moreover, Jpn. Pat. Appln. KOKOKU Publication No. 2-54734 discloses a cover which covers the insertion portion of an endoscope and has a channel formed therein for inserting therethrough a medical treatment tool.

Deformable relatively-soft components, such as a coating member for a bendable portion and a flexible tube, etc., are generally provided rearward of a tip structure constituting a tip portion of the insertion portion of an endoscope. In the conventional endoscope of the tip-cover detachable type, such soft components are liable to be cut or have holes pierced at the time of the tip cover being attached to or detached from the tip structure.

In the cases of Jpn. UM Appln. KOKAI Publication No. 51-103891 and Jpn. Pat. Appln. KOKOKU Publication No. 2-54734, where substantially the entire insertion portion of the endoscope is covered with a long cover, it is necessary to detach and clean the cover after the endoscope is used, but it is not necessary to clean the insertion portion itself since the insertion portion is not contaminated by virtue of the cover. However, attachment or detachment of the long cover to or from the insertion portion is not easy. Cleaning of the long cover is also not easy.

In a case where a disposable long cover is used, a person (patient) to be examined must bear its relatively high expense. In other words, the treatment bill is inevitably increased.

Furthermore, in the case of Jpn. Pat. Appln. KOKAI Publication No. 4-314439 where a hard tip cover is mounted on a hard tip structure, looseness may occur between the tip cover and the tip structure because it is difficult to sufficiently fit hard components to each other. If the looseness therebetween causes misalignment therebetween during a medical treatment using the endoscope, the field of view of the endoscope may be narrowed by the tip cover.

If the tip cover is firmly fixed to the tip structure and there is no play therebetween, detachment of the former from the latter is extremely difficult. Therefore, an excessive force must be applied to the tip cover to attach the tip cover to the tip structure or detach the same therefrom. As a result, it is highly possible that the tip cover mat be damaged or deformed.

SUMMARY OF THE INVENTION

This invention has been developed under the above-described circumstances, and it is an object of the present invention to provide an endoscope apparatus, in which relatively soft components, such as a coating member of a bendable portion a flexible tube, etc. located rearward of a tip structure body, can be protected from damage such as cutting or in which hole piercing, or a tip cover can be protected from breakage or deformation at the time of attaching or detaching the tip cover to or from the tip structure body which constitutes a tip portion of the insertion portion. In addition, it is an object of the present invention to provide a tip cover that can easily be attached or detached, and a joint portion between the tip structure body and the tip cover that has no looseness.

To attain these objects, the endoscope apparatus of the present invention, which is equipped with an insertion portion to be inserted into a body cavity, and a tip structure constituting a tip portion of the insertion portion, comprises: a tip cover detachably mounted onto the tip structure from the side of a tip portion of the tip structure, thereby covering the tip structure; engagement means provided on the insertion portion and detachably engaging the tip cover; and finger-driven means provided on that portion of the insertion portion which is in the vicinity of the engagement means, wherein the finger-driven means is used for attaching and detaching the tip cover.

Since the operator attaches or detaches the tip cover to or from the tip structure body located at the tip of the insertion portion with the finger-driven portion grasped by the fingers of one hand, cutting of components located rearward of the tip structure body and cutting of the tip cover is prevented. Further, the tip cover can easily be attached or detached by elastically deforming the same.

Since as described above, the finger-driven portion is provided on that portion of the insertion portion which is located in the vicinity of the engagement portion, relatively soft components, such as a coating member of the bendable portion, a flexible tube, etc. located rearward of a tip structure body, can be protected from damage such as cutting or hole piercing, or a tip cover can be protected from breakage or deformation at the time of attaching or detaching the tip cover to or from the tip structure body located at the tip of the insertion portion. In addition, the tip cover can easily be attached or detached, and a joint portion between the tip structure body and the tip cover does not have any looseness.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a longitudinal sectional view, showing an essential part of an endoscope according to a first embodiment of the invention;

FIG. 2 is a schematic view, showing the entire structure of an electronic endoscope;

FIG. 8 is an exploded perspective view, showing a end portion of an insertion portion of the endoscope;

DETAILED DESCRIPTION OF THE PREFERRED EMBODIMENTS

Figure 3:
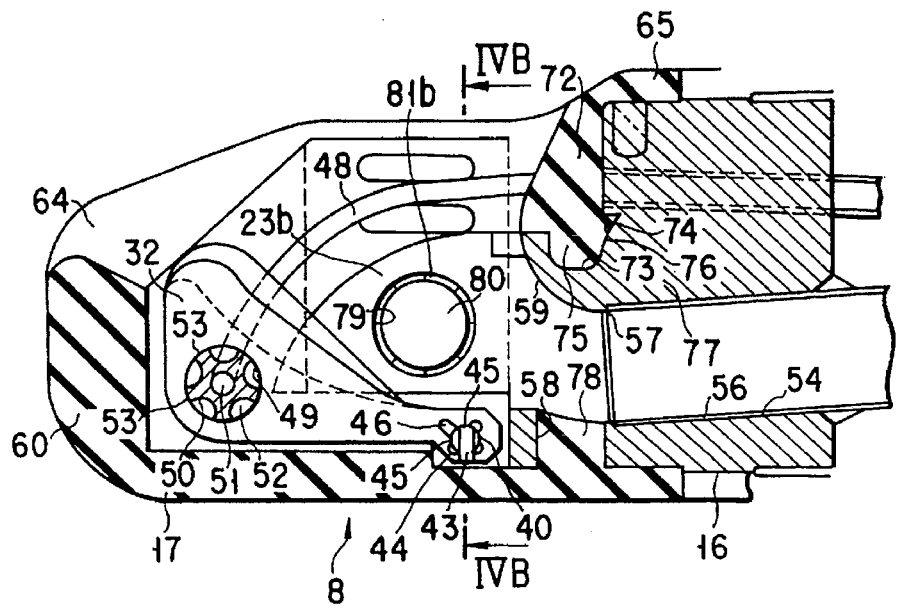
FIG. 3 is a longitudinal sectional view, showing a state in which a forceps-raising table is assembled.

An endoscope apparatus according to a first embodiment of the invention will be explained with reference to FIGS. 1–5D. FIG. 2 shows the entire system of an electronic endoscope apparatus 1. The electronic endoscope apparatus 1 has an electronic endoscope 2 equipped with photographing means, a light source unit 3 for applying illumination light to the endoscope 2, a video processor 4 for processing an image signal output from the endoscope 2, and a monitor 5 for displaying an image corresponding to the signal processed by the video processor 4.

The electronic endoscope 2 has an insertion portion 6 to be inserted into a body cavity to be examined. The insertion portion 6 includes a flexible tube portion 7, a tip structure portion 8, and a bendable portion 9 interposed between the tip structure portion 8 and the flexible tube portion 7.

Further, a hand-driven operating unit 10 is coupled with the proximal end of the flexible tube portion 7. The hand-side operating unit 10 has an operating nob 11 for curving the bendable portion 9 to direct an end portion of the insertion portion 6 in a desired direction, and a forceps-raising-table operating lever 12 for raising and lowering a forceps-raising table 22 (hereinafter explained) by means of an operating wire, etc. The operating unit 10 is coupled with the proximal end of a universal cord 13 having a distal end coupled with a connector 14.

The universal cord 13 is connected to the light source unit 3 by means of the connector 14, and also to the video processor 4 by means of a coupling cord 15 coupled with the connector 14.

As is shown in FIG. 1, the tip structure portion 8 of the insertion portion 6 of the endoscope 2 has a tip structure body 16 made of a metal (e.g. stainless steel) with high resistance against corrosion, and a tip cover 17 made of an elastic material and covering the outer periphery of the tip structure body 16.

Figure 5A:
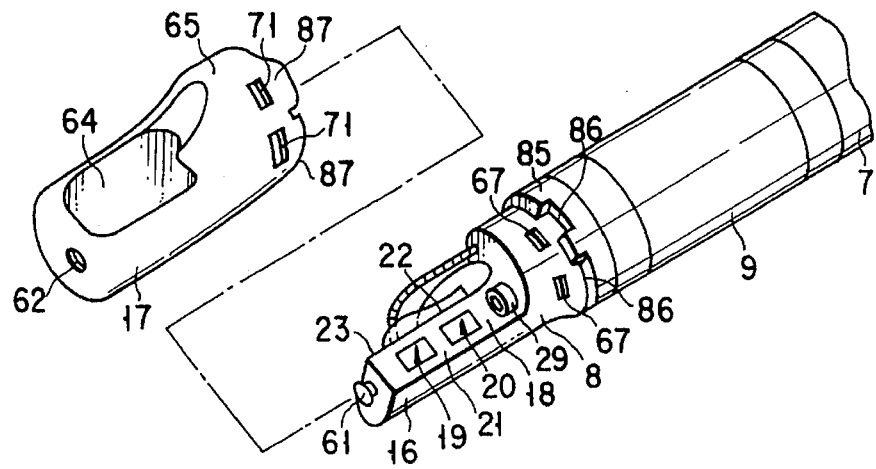
FIG. 5A is a perspective view, showing a state in which a tip cover is removed from a tip structure of the endoscope.

A substantially-flat circumferentially-recessed portion 18 is formed as a front portion of the tip structure body 16. As is shown in FIG. 5A, an optical-system mounting portion 21 and a forceps-mounting table receiving hole 23 (see FIG. 3) are formed at and in the recessed portion 18. An illumination optical system 19 and a photographing optical system 20 are mounted in the optical-system mounting portion 21, while the aforementioned forceps-raising table 22 is mounted in the hole 23.

An illumination lens 24 incorporated in the illumination optical system 19 and a photographing lens 25 incorporated in the optical system 20 are arranged in the optical-system mounting portion 21 along the axis of the insertion portion 6. The hole 23 receiving the forceps-raising table 22 is formed on one side of the portion 21 in which the lenses 24 and 25 are arranged in parallel.

The light-emitting portion of a light guide fiber 26 is located in the optical-system mounting portion 21 below the illumination lens 24. The light guide fiber 26 extends to the light source unit 3 through the insertion portion 6 of the endoscope 2, the operating unit 10 and the universal cord 13. When illumination light emitted from the light source unit 3 has entered the light-receiving end of the light guide fiber 26, it is transmitted through the fiber 26 to the tip structure body 16 and emitted therefrom to the outside.

The photographing optical system 20 includes a lens unit 27 for the photographing lens 25, and a photographing unit 28 such as a CCD for converting an image of an object formed by the lens unit 27 to an electric signal. An output signal from the photographing unit 28 is input to the video processor 4 via a lead wire extending through the insertion portion 6 of the endoscope 2, the operating unit 10 and the universal cord 13. The video processor 4 in turn outputs a signal to the monitor 5, where an image corresponding to the signal is displayed.

An air/water feeding nozzle 29 is located in the vicinity of the photographing lens 25 in the tip structure body 16. The body 16 has an air/water feeding hole 30 formed therein. An air/water feeding pipe 31 is fitted in the hole 30. The nozzle 29 is formed integral as one body with an end portion of the pipe 31.

The proximal end of the pipe 31 projects from the rear end face of the tip structure body 16 into the insertion portion 6. An air/water feeding pipe line 32 is coupled with the projection end of the pipe 31.

At the time of assembling the air/water feeding nozzle 29, the nozzle 29 is inserted into the air/water feeding hole 30 of the tip structure body 16 from the tip side of the hole, and then a boundary portion between the body 16 and the nozzle 29 is fixed by means of a filling material 33 such as an adhesive. As a result, bacteria and/or dirt are prevented from entering the clearance between the body 16 and the nozzle 29. A cleaning brush of an extremely small diameter can be inserted into the nozzle 29.

An opening 34 receiving the light guide fiber 26 of the illumination optical system 19 is formed in the lower surface of the tip structure body 16. The opening 34 is covered with a cover 35 made of an insulating material such as a synthetic resin, etc. The cover 35 is fixed to the body 16 around the opening 34.

An engagement projection 36 engaged with the tip cover 17 is formed integral with the cover 35 as one body and projects therefrom. The cover 35 may be formed of a metal member such as an aluminum die cast, etc., and fixed to the tip structure body 16 by means of solder.

Figure 4A:
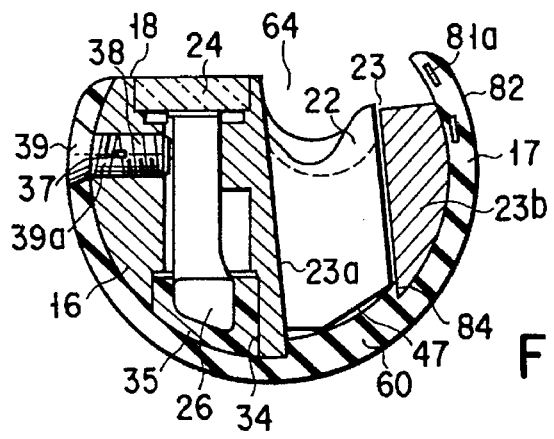
FIG. 4A is a sectional view, taken long line IVA—IVA of FIG. 1.

As is shown in FIG. 4A, a screw hole 37 is formed in the tip structure body 16, and the light emitting end of the light guide fiber 26 is fastened to the body 16 by means of a fastening screw 38 inserted in the screw hole 37.

A proximal end screw portion 39a of an engagement member 39 of the tip cover 17 is screwed in the screw hole 37, thereby engaging the tip cover 17 with the tip structure body 16. The engagement member 39 is formed of an insulating member.

As is shown in FIG. 3, the forceps-raising table 22 has its proximal end rotatably supported, by a raising pin 40, on that side wall surface 23a of the forceps-raising table receiving hole 23 of the tip structure body 16, which is located close to the optical-system mounting portion 21.

Figure 4B:
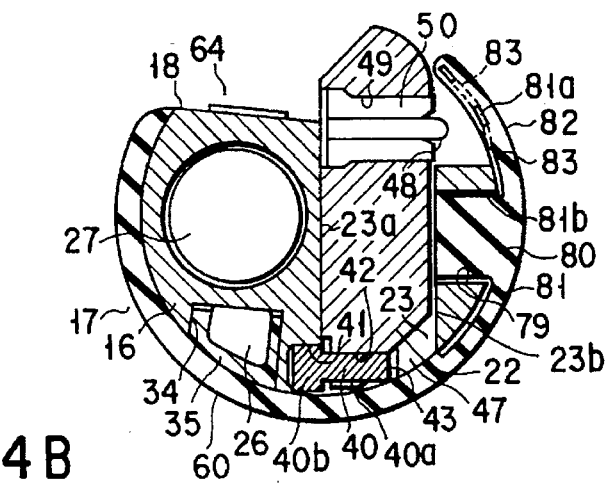
FIG. 4B is a sectional view, taken long line IVB—IVB of FIG. 3.

As is shown in FIG. 4B, a fixing hole 41 fixing the raising pin 40 is formed in the side wall surface 23a of the tip structure body 16. The proximal end of the raising pin 40 is fitted in the hole 41 and firmly fixed therein by means of a solder or an adhesive.

A raising hole 42 is formed in the proximal end of the forceps-raising table 22. The table 22 is rotatably supported on the side wall surface 23a by the raising pin 40 of a cantilever structure, with the projection 40a of the raising pin 40 (which projects from the fixing hole 41) fixed in the raising hole 42 of the table 22.

The raising pin 40 is located in the vicinity of the outer periphery of the tip structure body 16, and has a relatively short length so as not to project from the body 16. Fixing only one end of the raising pin 40 to the side wall surface 23a (i.e., using the raising pin 40 as a cantilever) enables the length of a sliding portion between the table 22 and the raising pin 40 to be made relatively long. As a result, the looseness of the table 22 can be prevented during its operation, as compared with a case where the both opposite ends of the raising pin 40 are supported and the length of the sliding portion between the table 22 and the raising pin 40 is relatively long.

Further, the fixing portion 40b of the raising pin 40 which is fixed in the fixing hole 41 of the tip structure body 16 is set to have a diameter larger than that of the projection 40a projecting from the fixing hole 41. Therefore, the run-out of the raising pin 40 is prevented, and its strength is increased.

The tip of the raising pin 40 has a stop portion 43 for preventing the forceps-raising table 22 from being disengaged from the raising pin 40. As is shown in FIG. 3, a plurality of continuous grooves 44 for injecting a decontaminating liquid are formed in the forceps-raising table 22 around the raising hole 42. The ends of portions between the grooves 44 constitute a plurality of contact portions 45 which connect the raising hole 42 of the table 22 to the raising pin 40. By virtue of the structure in which the raising pin 40 contacts the table 22 via the contact portions 45, looseness therebetween can be prevented.

One of the grooves 44 consists of a groove 46 larger and deeper than the stop portion 43 formed at one end of the raising pin 40. The stop portion 43 and the deep groove 46 are arranged so that the forceps-raising table 22 cannot be disengaged from the raising pin 40 during normal rotation of the table 22 for, for example, a raising operation. The table 22 has a lower portion 47 formed by cutting therefrom a lower portion other than the portion engaged with the raising pin 40.

A circular coupling hole 49 is formed in an end portion of the table 22, and receives a coupling shaft 50 secured to an end portion of a raising operation wire 48 such that it can slide therein. A wire stop hole 51 is formed in an axial portion of the coupling shaft 50, and receives therein the end portion of the raising operation wire 48.

A plurality of substantially semicircular grooves 52 for injecting a decontaminating liquid are formed in circumferential portions of the outer periphery of the coupling shaft 50. The ends of portions between the semicircular grooves 52 constitute a plurality of contact portions 53 which connect inner peripheral portions of the coupling hole 49 to the coupling shaft 50. The contact portions 53 prevent looseness between the forceps-raising table 22 and the coupling shaft 50. It is desirable to set the depth of each groove 52 to 0.2 mm or more so as to facilitate to inject the decontaminating liquid therein.

The proximal end of the raising operation wire 48 is coupled with the forceps-raising-table operating lever 12 of the operating unit 10. In accordance with the operation of the lever 12, the raising operation wire 48 is pulled to rotate the forceps-raising table 22 from a retreat position as shown in FIG. 3 to a forceps raising position as shown in FIG. 4B.

A forceps-channel connecting hole 54 which communicates with the receiving hole 23 of the table 22 is formed in the tip structure body 16. An end portion of a forceps-channel connecting pipe 56 is inserted and fixed in the connecting hole 54 such that it abuts the tip structure body 16. A clearance 57 between the body 16 and the end portion of the pipe 56 is filled with an adhesive.

A work hole 58 is formed in the tip structure body 16 between the forceps-raising table 22 and the forceps-channel connecting pipe 56. The hole 58 is provided for enhancing the efficiency of work for filling the clearance 57 with the adhesive.

An arcuate guide portion 59 extends into an upper region of the work hole 58, for guiding a forceps which extends toward the forceps-raising-table receiving hole 23 through the forceps-channel connecting pipe 56. The arcuate guide portion 59 is made of a metal with high corrosion resistance, such as a stainless steel, and formed integral with the tip structure body 16 as one body. Therefore, the portion 59 is free from abrasion due to insertion and removal of the forceps during raising the forceps-raising table 22.

The tip cover 17 of the tip structure body 16 is made of a material, such as silicon rubber, a fluorine-contained rubber, etc., which has high heat resistance necessary to bear autoclave sterilization, high adaptability to organ, high electric insulation and high tearing strength.

The tip cover 17 has a substantially cylindrical cover body 60 which can be inserted into and removed from the tip structure body 16 from its end portion. The cover body 60 has an end portion provided with an engagement hole 62 to be engaged with a tip cover engagement projection 61 projecting from the tip end of the tip structure body 16.

The engagement projection 61 projects from the end portion of the tip structure body 16 which is located eccentric with the axis of the tip structure body 16. The projection 61 has a head portion 61a, an intermediate portion 61b of a diameter smaller than that of the head 61a, and a male screw portion 61c continuously extending from the intermediate portion 61b and screwed in a screw hole 63 formed in the end surface of the tip structure body 16.

The engagement hole 62 of the cover body 60 has a large-diameter region 62a engaged with the head portion 61a of the projection 61, and a small-diameter region 62b engaged with the intermediate portion 61b of the projection 61.

To impart to the cover body 60 of the tip cover 17 good detachability and a strength sufficient to be kept free from damage during use, the hardness of the rubber is set to a value of 40°–80°, optimally 70°, and its thickness is set to a value of about 0.05–3 mm. The ratio of the inner diameter of the cover body 60 to the outer diameter of the tip structure body 16 is set to 0.7–1. The thus-constructed tip cover 17 is elastically fastened to the tip structure body 16, and therefore is free from looseness, slippage or unintentional detachment.

An opening 64 is formed in the portion of the cover body 60 which corresponds to the optical-system mounting portion 21 and the forceps-raising-table receiving hole 23 of the tip structure body 16. Through the opening 64, the illumination lens 24 and the photographing lens 25 mounted in the mounting portion 21, and the hole 23 are exposed to the outside.

The cover body 60 has a ring-shaped coupling portion 65 located at its rear end and serving an insertion portion. The coupling portion 65 has a width of at least 0.2 mm or more, and extends to a portion in the vicinity of a joint between the bendable portion 9 and the tip structure body 16. Thus, the entire coupling portion 65 is firmly secured to the entire joint.

The tip structure body 16 also has an engagement portion 66 detachably engaged with the insertion portion of the cover body 60 of the tip cover 17. The engagement portion 66 has a pair of engagement projections 67, as well as the engagement projection 36 engaged with the cover 35 in the light guide fiber-receiving opening 34, and the engagement member 39 in the screw hole 37.

Figure 5B:
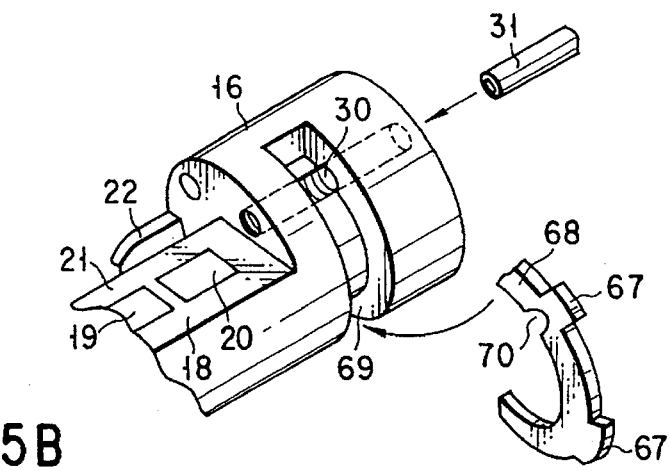
FIG. 5B is a perspective view, showing a state in which a fixing member and a tube line pipe are removed from the tip structure.
Figure 5C:
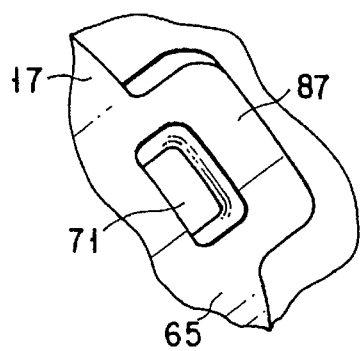
FIG. 5C is a perspective view, showing an engagement hole formed in the tip cover.

As is shown in FIG. 5B, the engagement projections 67 project from edge portions of a substantially arcuate fixing member 68, which is fitted in an arcuate fixing groove 69 formed in an outer peripheral surface of the tip structure body 16.

The fixing groove 69 is formed across the air/water feeding hole 30 in which the air/water feeding pipe 31 is fitted. At the time of fitting the pipe 31 in the hole 30, the pipe 31 is inserted through the tip structure body 16, and then a filler such as an adhesive is filled in a water-tight manner between that portion of the fixing groove 69 in which the pipe 31 is exposed and the tip structure body 16.

The fixing member 68 has a depression 70 which receives that portion of the air/water feeding pipe 31 which projects from the fixing groove 69. Thus, the fixing member 68 is fitted in the relatively deep fixing groove 69 without adversely affecting the contents of the tip structure body 16, with the result that the fixing member 68 is firmly fixed.

As is shown in FIG. 5A, the engagement projections 67 are detachably engaged with engagement holes 71 formed in the tip cover 17. Each projection 67 has a height substantially equal to the level of the outer periphery of the tip cover 17.

Figure 5D:
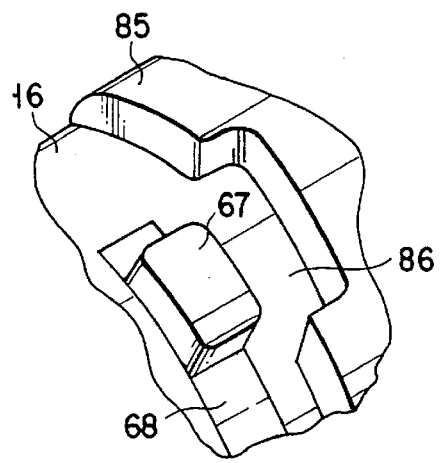
FIG. 5D is a perspective view, showing an engagement projection formed on the tip cover.

As is shown in FIG. 5D, each projection 67 has a shape of a wedge with a larger outer cross section and a smaller inner cross section. Accordingly, each engagement hole 71 of the tip cover 17, which receives the projection 67, has a shape of a wedge with a larger outer width and a smaller inner width. Where the projection 67 and the hole 71 are once engaged with each other, they are hard to disengage.

Each of the engagement projections 67 is made of an insulating material such as a resin, ceramic, etc. such that its surface is electrically isolated from the tip structure body 16.

As is shown in FIG. 3, an insulating portion 72 is formed integral as one body with an inner end portion of the coupling portion 65 of the cover body 60 of the tip cover 17. The lower end of the insulating portion 72 is located on the curved guide portion 59 of the tip structure body 16. The insulating portion 72 prevents short-circuiting from occurring, for example, when high-frequency cutting has been performed using papillotomy knife, and the knife has been brought into contact with the tip structure body 16.

The insulating portion 72 has engagement projections 75 and 76 engaged with engagement depressions 73 and 74 formed in the tip structure body 16. The engagement projections and depressions constitute slippage-preventing means 77 for preventing the portion 72 from slipping at the time of a treatment tool being inserted into the body 16.

A projection 78, which projects from the tip cover 17, is received in the work hole 58 of the tip structure body 16. The projection 78 prevents the tip cover 17 from slipping from the body 16, and also prevents the treatment tool from being caught by an edge portion of the work hole 58 at the time of the tool being inserted into the forceps channel.

As is shown in FIG. 4B, the tip structure body 16 has an engagement hole 79 formed in a side wall surface 23b, opposite to the side wall surface 23a, of the optical-system mounting portion 21 for guiding the forceps-raising table 22. The engagement hole 79 constitutes slippage-preventing means for preventing the tip cover 17 from coming off the body 16. An engagement projection 80 projecting from the inner periphery of the tip cover 17 is engaged with the engagement hole 79.

A relatively-hard reinforcing member 81 is fitted in an outer peripheral portion of the engagement projection 80. The reinforcing member 81 has a portion 81a buried in that thin portion 82 of the tip cover 17, which is provided near the forceps-raising table 22 and defines part of the edge of the opening 64; and a cylindrical fitting portion 81b fitted in the outer periphery of the engagement projection 80.

The reinforcing member 81 is formed of a metal or resin with high corrosion resistance by pressing or molding, and preferably has a thickness of 0.1–1 mm. The member 81 is partially buried in the tip cover 17.

The buried portion 81a of the reinforcing member 81 has a hole 83. At the time of partially burying the member 81 into the tip cover 17, the rubber constituting the tip cover 17 fills the hole 83, thereby increasing the peel strength between the tip cover 17 and the reinforcing member 81.

Since the buried portion 81a of the reinforcing member 81 is fitted in the engagement hole 79, the engagement projection 80 is not easily deformed. As a result, the tip cover 17 is prevented from easily coming off the tip structure body 16.

The buried portion 81a of the reinforcing member 81 not only prevents the member 81 from slipping or coming off the tip cover 17 during use, but also prevents the tip cover 17 from being displaced in the axial direction or rotational direction. Accordingly, the thin portion 82 of the tip cover 17, provided near the forceps-raising table 22 and defining the part of the edge of the opening 64, is prevented from being cut by the movement of the forceps-raising table 22, or from being held between the table 22 and the tip structure body 16, thereby causing malfunction of the table 22.

As is shown in FIG. 4A, a rib 84, which inwardly projects from an inner peripheral surface of the tip cover 17, is received in the forceps-raising-table receiving hole 23 of the tip structure body 16. The rib 84 is located corresponding to the cutout 47 of the forceps-raising table 22, and prevents displacement of the tip cover 17 in the direction of rotation.

A hard finger-driven member 85 to be used to attach and detach the tip cover 17 is provided over the entire periphery of the insertion portion 6 in the vicinity of the joint between the bendable portion 9 and the tip structure body 16 and in the vicinity of the engagement portion 66 of the tip cover 17. The member 85 is made of a material having electrically insulating properties, such as a synthetic resin, ceramics, etc., and has a thickness of about 0.1–3 mm.

Depressions 86 for positioning are formed in those portions of the member 85 which correspond to the engagement projections 67 of the fixing member 68. The depressions 86 are detachably engaged with projections 87 projecting from rear end portions of the coupling portion 65 of the cover body 60 of the tip cover 17.

The member 85 has a color different from the tip cover 17 so that the former can easily be discriminated from the latter. A concave stepped portion 88 is formed in the outer periphery of a proximal end portion of the member 85. A bendable cover member 89 has an end portion wound by a fixing thread 90 and fixed in contact with the proximal end of the member 85. The structure fixed by the thread is coated with an adhesive, thus forming a fixing portion 91. The concave stepped portion 88 is filled with the adhesive, providing the fixing portion 91 with sufficient water-tightness.

Although in the above embodiment, the engagement projections 67 are separated from the member 85, they may be formed integral as one cylindrical body, and further the light guide fiber 26 and the cover 35 received in the opening 34 may be formed integral as one body.

The operation of the above-described structure will now be explained. First, the procedure for attaching the tip cover 17 to the tip structure body 16 will be explained. At the time of attaching the cover 17, the operator grasps the finger-driven member 85 of the insertion portion 6 of the endoscope 2 by the fingers of one hand, and the tip cover 17 by the fingers of the other hand. Then, he aligns the tip cover 17 with the tip structure body 16, and attaches the former to the latter.

Subsequently, the operator grasps the thin portion 82 provided near the forceps-raising table 22 and defining the part of the edge of the opening 64, and engages the engagement projection 80 with the engagement hole 79 in the tip structure body 16, thereby fixing the former to the latter.

Then, the tip-cover-engaging projection 61 of the tip structure body 16 is engaged with the engagement hole 62 in the tip cover 17. Further, the projection 78 is inserted into the working hole 58 in the body 16, and lastly the engagement projection 36 of the cover 35 in the light guide fiber-receiving opening 34, the engagement member 39 in the screw hole 35 and the engagement projections 67 are inserted into the engagement hole 71 in the tip cover 17.

On the other hand, at the time of detaching the tip cover 17 from the tip structure body 16, firstly the engagement projection 36 of the cover 35 in the light guide fiber-receiving opening 34, the engagement member 39 in the screw hole 35 and the engagement projections 67 are detached from the engagement hole 71 in the tip cover 17.

Thereafter, the thin portion 82 of the tip cover 17 provided near the forceps-raising table 22 and defining the part of the edge of the opening 64 is grasped, thereby detaching the engagement projection 80 from the engagement hole 79 in the tip structure body 16. Further, the projection 78 is detached from the working hole 58 in the body 16, and the tip cover 17 is pulled from the body 16, thereby detaching the tip cover engagement projection 61 from the engagement hole 62 in the tip cover 17.

The above-described structure has the following advantages:

The hard finger-driven member 85 to be used to attach and detach the tip cover 17 is provided over the entire periphery of the insertion portion 6 in the vicinity of the joint between the bendable portion 9 and the tip structure body 16 and in the vicinity of the engagement portion 66 of the tip cover 17. Therefore, the operator can detach the tip cover 17 from the tip structure body 16 with the member 85 grasped by the fingers, at the time of performing cleaning or decontamination after each medical examination. Therefore, there is no danger of the operator's injuring, with his nails, etc., or making a hole in relatively soft components such as the cover member 89 of the bendable portion 9 located in rear of the tip structure portion 8, the flexible tube portion 7, etc., or damaging or deforming the tip cover 17.

Moreover, making the member 85 have a color different from the tip cover 17 or the cover member 89 enables the operator to easily discriminate the boundary between the tip cover 17 and the finger-driven member 85. As a result, the attachment and detachment of the tip cover 17 is facilitated, thereby enhancing the operability of the endoscope apparatus.

Further, since the insulating portion 72, which is located on the curved guide portion 59 of the tip structure body 16, is formed integral with the inner end portion of the coupling portion 65 of the cover body 60 of the tip cover 17, the wall of the endoscope is prevented from being adversely affected by high frequency, etc.

In addition, since the depressions 86 for positioning are formed in those portions of the member 85 which correspond to the engagement projections 67 of the fixing member 68, the engagement hole 71 in the tip cover 17 can have a large size and a sufficient strength.

Since the buried portions 81a of the reinforcing member 81 are buried in the thin portion 82 of the tip cover 17 provided near the forceps-raising table 22 and defining the part of the edge of the opening 64, the tip cover 17 is prevented from being held between the table 22 and the tip structure body 16, and hence the endoscope can be used safely.

Since the reinforcing member 81 can be engaged with the tip structure body 16, the member 81 is prevented from slipping out of the tip cover 17. Furthermore, the reinforcing member 85 is partially buried in the tip cover 17, it is prevented from coming off the same. The engagement portion of the reinforcing member 81, which is constituted by the fitting portion 81b, is prevented from being removed even by repeated attachment/detachment of the tip cover 17.

Since the raising pin 40 has its one end fixed to the side wall surface 23a and the other end free (i.e., the pin 40 is used as a cantilever), the length of the slide portion between the pin 40 and the forceps-raising table 22 can be lengthened as compared with the case where the both ends of the pin 40 are fixed, thereby making the table 22 free from looseness and facilitating cannulation.

The fixing portion 40b of the raising pin 40, securely fitted in the fixing hole 41 in the tip structure body 16, has an outer diameter larger than the projection 40a of the pin 40, projecting from the hole 41. Therefore, the pin 40 has a high joint strength and a high join strength and a high bending strength.

Since the curved guide portion 59 at the outlet of the forceps is formed integral with the tip structure body 16 made of a metal, and the insulating portion 72 is provided on the guide portion 59, the insulating portion 72 is prevented from being cut by the forceps, and an electrically-insulated endoscope can be made at low cost. Moreover, since the insulating portion 72 is formed integral with the cover body 60 of the tip cover 17, a more cheap endoscope can be provided. The slip-preventing means 77 provided between the tip structure body 16 and the insulating portion 72 prevents the slip of the portion 72 when a treatment tool such as the forceps is inserted or pulled.

The ring-shaped coupling portion 65 is provided over the entire periphery of the insertion portion of the cover body 60 of the tip cover 17. Therefore, the cover body 60 is firmly fixed to the tip structure body 16. Further, since the inserting end of the tip cover 17 is located nearer to the tip of the endoscope than the bendable portion 9, the cover 17 does not adversely affect the curving operation of the endoscope.

The fixing portion between the tip cover 17 and the tip structure body 16 can prevent slip of the cover 17, thereby enabling a stable medical examination. The fixing means consists of convex portions provided on the tip structure body 16, such as the engagement projection 36 of the cover 35, the engagement member 39, the engagement projections 67, etc., and the hole 71 formed in the tip cover 17. Therefore, the completion of the attachment of the tip cover 17 to the body 16 can easily be confirmed. Furthermore, the convex portions provided on the tip structure body 16, such as the engagement projection 36 of the cover 35, the engagement member 39, the engagement projections 67, etc. are fitted in the hole 71 in the tip cover 17. Thus, the tip cover 17 has an even outer surface.

The arcuate fixing groove 69 is formed in a remaining portion of the tip structure body 16, and the engagement projections 67 are provided on the insulating fixing member 68 fitted in the groove 69. This being so, it is not necessary to enlarge the outer diameter of the tip structure body 16 so as to form a groove or hole therein, with the result that the body 16 can be made thin.

The tip cover 17 and the tip structure body 16 are fixed to each other by means of at least two fixing means provided at open end portions of the tip cover 17, thereby preventing the peel off of the cover 17. Further, since the fixing means fixing the tip cover 17 and the tip structure body 16 are provided at remaining open end portions of the cover 17, relatively large engagement means can be used to firmly fix the same.

Since the fixing means fixing the tip cover 17 and the tip structure body 16 are located on outer peripheral portions of the body 16 close to the photographing optical system 20, the field of view of the photographing optical system 20 can be prevented from being narrowed as a result of slip of the tip cover 17. The fixing means formed by burying the engagement member 39 in the screw hole 37 does not require any particular working for forming the member 39, and hence can be made at low cost. Also, the combination of the various fixing means such as the engagement projection 36 of the cover 35, the engagement member 39, the engagement projections 67, etc. can increase the strength of fixing.

Since a plurality of continuous grooves 44 for injecting a decontamination liquid are provided in a peripheral slide portion of the raising hole 42 receiving the forceps-raising pin 40, the slide portion can be decontaminated and hence kept in a sanitary condition. More specifically, since the slide portion is the peripheral surface of the hole 42, it is not necessary to further reduce the diameter of the thin raising pin 40, and therefore the strength of the pin 40 can be secured.

A plurality of semicircular grooves 52 formed for injecting a decontamination liquid in the outer periphery of the coupling shaft 50 inserted in the coupling hole 49 of the forceps-raising table 22 enable decontamination of the slide portion between the coupling hole 49 and the coupling shaft 50. As a result, the slide portion is kept in a sanitary condition. Since the grooves 52 are formed in the outer periphery of the coupling shaft 50, they can easily be formed.

Since the ratio of the inner diameter of the tip cover 17 to the outer diameter of the tip structure body 16 is set to 0.7–1, The tip cover 17 can be firmly secured to the tip structure body 16. In addition, since the ring-shaped coupling portion 65 is provided over the entire periphery of a rear end portion of the tip cover 17, the tip cover 17 can be firmly fixed to the tip structure body 16.

Further, the portion of the tip cover 17 which is located in the vicinity of the engagement hole 71 is a weakest portion in the cover. The cover 17 can be protected from damage by lastly engaging this portion with the tip structure body 16 at the time of attaching the cover to the body, and by firstly disengaging the same portion from the body at the time of detaching the cover from the body.

The finger-driven member 85 provided between the tip cover 17 and the fixing portion 91 facilitates assembling performed with the bendable cover member 89 rendered to abut against the finger-driven member 85, i.e., fixing work using the fixing thread 90 of the bendable cover member 89. Furthermore, an adhesive adhered to the fixing portion 91 is prevented from flowing into the joint surface between the tip cover 17 and the tip structure body 16, with the result that the attaching/detaching of the cover is prevented from being adversely affected.

Figure 6:
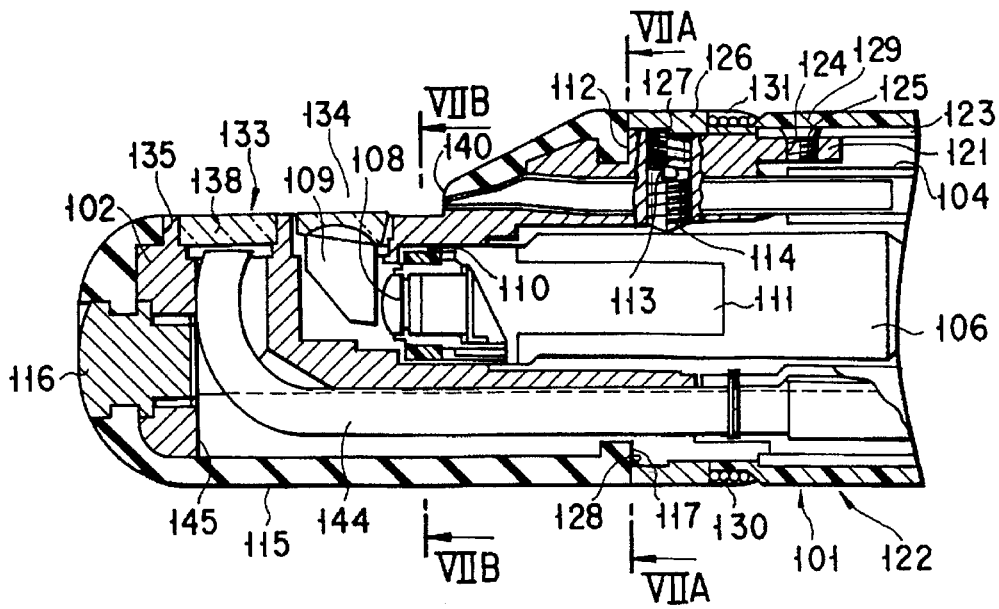
FIG. 6 is a longitudinal sectional view, showing an essential part of an endoscope according to a second embodiment of the invention.

FIGS. 6–8 show a second embodiment of the invention. FIG. 6 shows a tip end of an insertion portion 101 of an endoscope. Reference numeral 102 denotes a tip structure body. As is shown in FIG. 8, the tip structure body 102 is coupled with a forceps channel 103, a air/water feed channel 104, a guide channel 105 for a forceps-raising wire, etc.

The tip structure body 102 has a photographing hole 107 formed therein and receiving a photographing unit 106. The photographing unit 106 contains an optical lens 108, and has a fitting portion 110 for aligning the optical axes of the optical lens 108 and a photographing optical lens 109 located close to the front end of the tip structure body 102, and a fixing portion 111 formed integral with the fitting region 110 and which a screw contacts.

After inserted into the photographing hole 107, the photographing unit 106 is fixed by a fixing screw 114 screwed through a screw hole 113 formed remoter from the front end of the tip structure body 102 than an engagement groove 112, which will be explained later. The screw hole 113 extends toward the center of the photographing unit 106, and the fixing screw 114 screwed through the screw hole 113 contacts the fixing portion 111, thereby preventing the photographing unit 106 from rotating relative to the tip structure body 102 at the time of fixing the unit 106.

As is shown in FIG. 6, the screw hole 113 is located remoter from the tip of the tip structure body 16 than the rear end of the tip cover 115 where the tip cover 115 is mounted on the tip structure body 16. A finger-driven member 126 or a coating member 129, which will be explained later, is provided outside the screw hole 113 to close the same. This structure can prevent a general user from easily unscrewing the fixing screw 114 in the screw hole 113, and rendering the photographing unit 106 displaced from a predetermined position and incapable of its observation operation. Moreover, leakage of water to the photographing unit 106 through the screw hole 113 can be prevented in a reliable manner.

An engagement projection 116 incorporated in a tip cover 115 and made of an elastic material is provided on a front end portion of the tip structure body 102. An annular rib 117 inwardly projects from a rear end portion of the tip cover 115.

The rib 117 is fitted in the engagement groove 112 when the tip cover 115 is attached to the tip structure body 102. The ratio of the width of the rib 117 to that of the groove 112 is set to about 0.7–1.3.

Figure 7A:
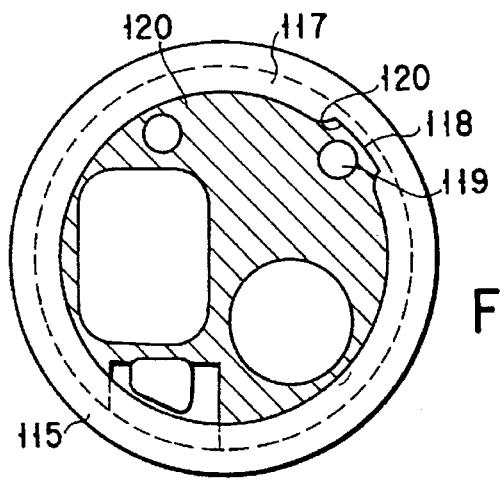
FIG. 7A is a sectional view, taken long line VIIA—VIIA of FIG. 6.

As is shown in FIG. 7A, the engagement groove 112 has a shallow portion 118 with a depth shallower than the other portion. If part of the elements contained in the tip structure body 102, for example, a communication passage 119 which communicates with the guide channel 105 for the forceps-raising wire, coincides with the engagement groove 112, the passage 119 will be located inside the shallow portion 118 of the groove 112 so as to avoid the groove.

The rib 117 of the tip cover 115 has a concave portion 120 located corresponding to the shallow portion 118 of the groove 112. As a result, the engagement groove 112 for engaging the tip cover 115 with the tip structure body 102 can be formed in the entire periphery of part of the body 102, thereby firmly engaging the tip cover 115.

A bendable-tube fixing portion 121 projects from the rear end of the tip structure body 102. The fixing portion 121 has a screw hole 124 formed therein. A bendable tube 123 which is incorporated in a bendable portion 122 coupled with the rear end of the tip structure body 102 in the insertion portion 101 is fixed to the fixing portion 121 by means of a fixing screw 125 screwed in a screw hole 124.

As is shown in FIG. 6, a hard finger-driven member 126 to be used for attaching/detaching the tip cover 115 is mounted on the entire periphery of that portion of the tip structure body 102 which is located on the rear side of the engagement groove 112. A stepped member 127 for positioning, which has a large-diameter front portion and a small-diameter rear portion, is provided on that outer peripheral portion of the tip structure body 102 which contacts the tip cover 115. The large-diameter front portion of the stepped member 127 positions the finger-driven member 126 when the member 126 is mounted on the outer periphery of the tip structure body 102 from the rear end thereof. The screw hole 113 is provided below the finger-driven member 126.

An adhesive 128 is applied on a boundary portion between a front end portion of the finger-driven member 126 and the tip structure body 102, thereby preventing dirt from invading between the member 126 and the body 102 and securing the water-tightness therebetween.

A front end portion of a cover member 129 made of an elastic material is fixed to the outer periphery of a rear end portion of the tip structure body 102, thereby covering the outer periphery of the bendable portion 122. The front end portion of the cover member 129 contacts a rear end portion of the finger-driven member 126, and is tightly wound by a thread 130 with an outer diameter φ of 0.1–0.5 mm (e.g. a cotton thread or a fish line). An adhesive 131 is applied to the thread 130 and firmly fixes the cover member 129 to the finger-driven member 126.

At the time of fixing the cover member 129 to the outer periphery of the tip structure body 102 by winding the thread 130 on the front end portion of the cover member 129, slippage of the finger-driven member 126 from the body 102 due to the elastic force of the cover member 129 of the bendable portion 122 can be prevented by a stepped portion 127 formed on an outer peripheral portion of the body 102. Further, the cover member 129 of the bendable portion 122 fixed on the outer periphery of the tip structure body 102 keeps the water-tightness.

Figure 7B:
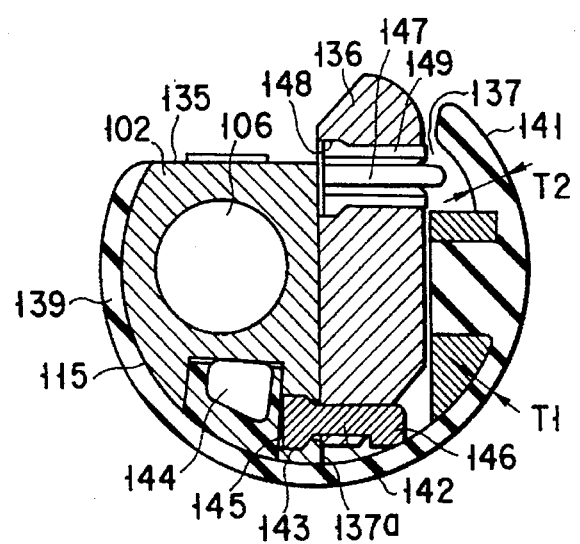
FIG. 7B is a sectional view, taken long line VIIB—VIIB of FIG. 6.

The tip structure body 102 has a substantially-flat circumferentially-recessed portion 132 which constitutes a front portion of the body 102. The recessed portion 132 has an optical-system mounting portion 135 in which an illumination optical system 133 and a photographing optical system 134 are mounted, and a hole 137 which receives a forceps-raising table 136 as shown in FIG. 7B. In the optical-system mounting portion 135, an illumination lens 138 incorporated in the illumination optical system 133 and a photographing lens 109 incorporated in the illumination optical system 133 are arranged along the axis of the insertion portion 101. The hole 137 receiving the forceps-raising table 136 is formed on one side of the optical-system mounting portion 135 in which the lenses 138 and 109 are arranged in parallel.

An opening 140 is formed in that portion of a cover body 139 incorporated in the tip cover 115, which corresponds to the optical-system mounting portion 135 and the forceps-raising-table receiving hole 137 of the tip structure body 102. Through the opening 140, the illumination lens 138 and the photographing lens 109 mounted in the mounting portion 135, and the forceps-raising-table receiving hole 137 are exposed to the outside.

As is shown in FIG. 7B, the tip cover 115 has a thick portion 141 formed near the forceps-raising table 136 and defining part of the edge of the opening 140. The thick portion 141 has a thickness T2 corresponding to 1.2–3 times the thickness T1 of another portion of the tip cover 115. Thus, the thick portion 141 of the cover 115 is prevented from unintentional movement during a medical examination, or from being held between the forceps-raising table 136 and the tip structure body 102.

As is shown in FIG. 7B, the proximal end of the forceps-raising table 136 is rotatably supported by a raising pin 142 secured to that side wall surface 137a of the tip structure body 102, which defines the forceps-raising-table receiving hole 137 and is located close to the optical-system mounting portion 135.

The raising pin 142 is fixedly fitted in a raising-pin receiving hole 143 formed in the tip structure body 102. A groove 145 for receiving a light guide fiber 144 is formed in the optical-system mounting portion 135 of the body 102. The hole 143 communicates the groove 145 with the hole 137.

The raising-pin receiving hole 143 has a large-diameter portion on the side of the light-guide-fiber receiving groove 145, and a small-diameter portion on the side of the forceps-raising-table receiving hole 137. The raising pin 142 is inserted into the raising-pin receiving hole 143 from the side of the groove 145, and secured therein by means of solder or an adhesive. Thus, the pin 142 is prevented from coming off the tip structure body 102. As in the case of the first embodiment, the pin 142 has a stop portion 146 for stopping slippage of the forceps-raising table 136.

A circular coupling hole 148 is formed in a distal end portion of the table 136, and receives an end portion of the raising operation wire 147 such that a coupling shaft 149 secured to the end portion of the wire 147 can slide therein.

A manner for mounting the tip cover 115 to the tip structure body 102 will be explained. First, the tip cover 115 is roughly attached to the body 102. Then, a front end portion of the tip cover 115 is engaged with the tip structure body 102 by means of engagement means of the body 102 such as the engagement projection 116, etc., and lastly, the rib 117 of the tip cover 115 is fitted in the engagement groove 112 in the body 102.

The above-described structure has the following advantages:

Since the tip cover 115 is mounted on the tip structure body 102 by fitting the rib 117 of the cover 115 into the engagement groove 112 formed in the body 102, it is not necessary to provide the body 102 with an engagement member such as an engagement projection made of an insulating material, etc., thereby reducing its manufacturing cost. Further, the tip cover 115 has a smooth surface, which protects a corporeal tissue from damage at the time of inserting the endoscope into a body cavity.

Moreover, the thick portion 141 of the tip cover 115 located near the forceps-raising table 136 and defining part of the edge of the opening 140 has the thickness T2 corresponding to 1.2–3 times the thickness T1 of another portion of the tip cover 115. Therefore, the edge of the tip cover 115, defining the opening 140, will not be held between the forceps-raising table 136 and the tip structure body 102 during a medical examination, thereby preventing malfunction of the table 136 and cut or other damages of the cover edge. Furthermore, since the thick portion 141 makes it unnecessary to provide the reinforcing member 81 in the tip cover 115 as in the first embodiment, the cover 115 can be produced at a lower cost than in the first embodiment.

In addition, if part of the elements contained in the tip structure body 102, for example, the communication passage 119 which communicates with the guide channel 105 for the forceps-raising wire coincides with the engagement groove 112, the passage 119 is arranged to extend in the shallow portion 118 of the groove 112 which is shallower than the other portion. Therefore, it is not necessary to enlarge the outer diameter of the tip structure body 102.

Figure 9:
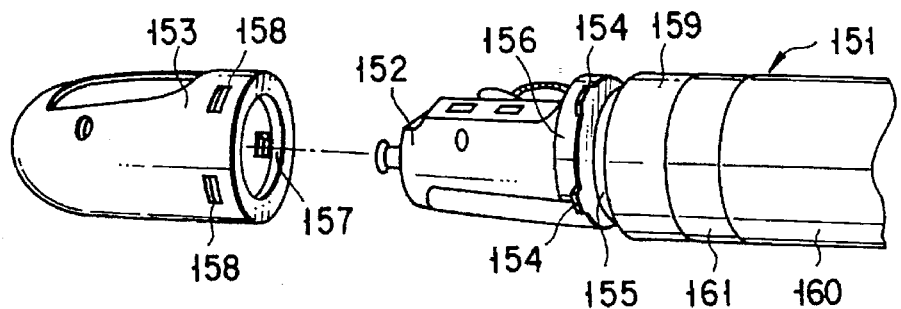
FIG. 9 is a perspective view, showing an essential part of a third embodiment of the invention.

FIG. 9 shows a third embodiment of the invention. In this embodiment, the structure of engagement members between a tip structure body 152 constituting a tip end portion of the endoscope and a tip cover 153 made of an elastic material and covering the outer periphery of the tip structure body 152 is formed by the combination of the engagement members employed in the first and second embodiments.

Specifically, in the third embodiment, the tip structure body 152 has a plurality of engagement projections 154 of an insulating material on the outer periphery of a rear end portion thereof, and an engagement annular groove 155 formed in the entire periphery of that portion of the body 152 which is located near the rear end portion and remoter than the same from the tip end of the body 152. An insulated portion 156 is provided in the vicinity of the engagement projections 154, thereby isolating a portion containing the projections 154 from the other portion of the tip structure body 152.

A rib 157 inwardly projects from the inner periphery of that front end portion of the tip cover 153 which corresponds to the engagement groove 155 of the tip structure body 152, and engagement holes 158 are formed in those portions of the tip cover 153 which correspond to the engagement projections 154.

A hard finger-driven portion 159 to be used to attach/detach the tip cover 153 is formed by coating an insulating material on the entire periphery of that portion of the tip structure body 152 which is located remoter than the engagement groove 155 from the tip end of the body 152.

Preferably, the relationship between the outer diameter C of the tip structure body 152, the outer diameter D of the engagement groove 155 and the inner diameter E of the rib 157 satisfies the following formula:

$$C > E, \ 0.5 \leq E/D \leq 1$$

Further, the relationship between the outer diameter C of the tip structure body 152 and the inner diameter F of the tip cover 153 is set to satisfy the following equation:

$$1 \leq F/C \leq 1.2$$

As a result, the tip cover 153 is prevented from easily slipping from the tip structure body 152. Reference numeral 160 designates a cover member of an elastic material covering the outer periphery of a cylindrical portion of an insertion portion 151 of the endoscope coupled with the tip structure body 152, reference numeral 161 designates a fixing portion of the cover member 160 fixed on the outer periphery of the tip structure body 152.

The above-described structure has the following advantages:

Since the hard finger-driven portion 159 for attaching/detaching the tip cover 153 is formed by coating a portion of the tip structure body 152 with an insulating material, it is not necessary to fix a separate finger-driven member of an insulating material to the tip structure body 152. As a result, the endoscope can have a small diameter and be made at low cost.

Moreover, since the engagement means between the outer periphery of the tip structure body 152 and the tip cover 153 has the structure obtained by combining the structures employed in the first and second embodiments, the body 152 and the cover 153 can be fixed more firmly, thereby preventing the cover 153 from coming off the body 152 during a medical examination.

Furthermore, since the relationship between the outer diameter C of the tip structure body 152 and the inner diameter F of the tip cover 153 is set to satisfy $1 \leq F/C \leq 1.2$, the attachability/detachability of the tip cover 153 to and from the tip structure body 152 can be enhanced. The inner diameter E of the rib 157 is smaller than the outer diameter C of the tip structure body 152, and hence there is no danger of the tip cover 153 coming off the tip structure body 152.

Figure 10:
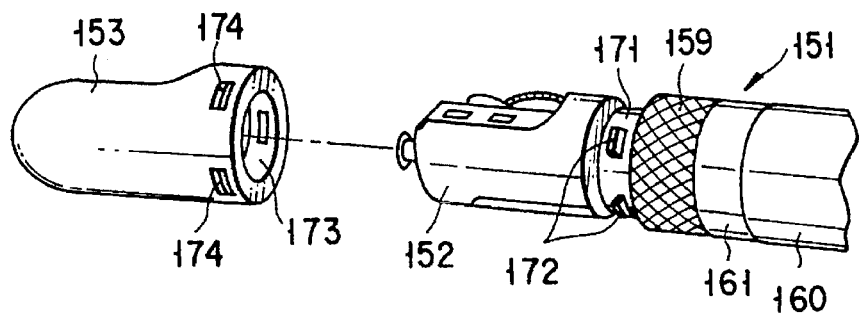
FIG. 10 is a perspective view, showing an essential part of a fourth embodiment of the invention.

FIG. 10 shows a fourth embodiment of the invention. This embodiment differs from the third embodiment in that a wide groove 171 which is wider than the engagement groove 155 is formed in the entire periphery of a rear end portion of the tip structure body 152, and engagement projections 172 for engagement of the tip cover 153 with the tip structure body 152 are provided such that they project from substantially central bottom portions of the wide groove 171.

Further, a wide rib 173 inwardly projects from the inner periphery of that rear end portion of the tip cover 153 which corresponds to the wide groove 171 in the tip structure body 152, and engagement holes 174 are formed in those portions of the tip cover 153 which correspond to the engagement projections 172 of the tip structure body 152.

Moreover, a hard finger-driven portion 159 to be used to attach/detach the tip cover 153 is formed by coating an insulating material on the entire periphery of that portion of the tip structure body 152 which is located remoter than the engagement groove 171 from the tip end of the body 152.

The above-described structure has the following advantages:

Since the hard finger-driven portion 159 for attaching/detaching the tip cover 153 is formed by coating a portion of the tip structure body 152 with an insulating material, it is not necessary to fix a separate finger-driven member of an insulating material to the tip structure body 152. As a result, a thin endoscope can be made at low cost.

Moreover, the fixing portion between the tip cover 153 and the tip structure body 152 can be made thick and strong, since it consists of the wide rib 173 inwardly projecting from the inner periphery of the rear end portion of the tip cover 153 which corresponds to the wide groove 171 in the tip structure body 152, and the engagement holes 174 formed in the portions of the tip cover 153 which correspond to the engagement projections 172 of the tip structure body 152. As a result, the fixing portion therebetween will not be damaged and cut during a medical examination, and accordingly the tip cover 153 will not unintentionally detach from the tip structure body 152.

Moreover, since there are provided the engagement projections 172 projecting from the substantially central bottom portions of the wide groove 171, and the engagement holes 174 formed in the rib 173 of the tip cover 153 and engaged with the projections 172, the outer diameter of the tip cover 153 can be thinned.

Figure 11:
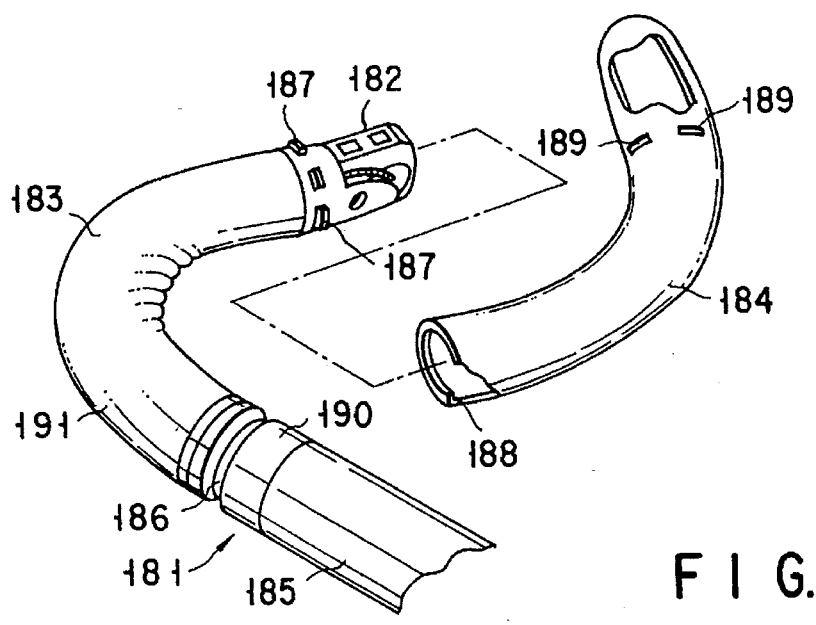
FIG. 11 is a perspective view, showing an essential part of a fifth embodiment of the invention.

FIG. 11 shows a fifth embodiment of the invention. This embodiment employs a tip structure body 182 which constitutes a tip portion of an insertion portion 181 of the endoscope, and a tip cover 184 of an elastic material having a length sufficient to cover a bendable portion 183 coupled with the rear end of the tip structure body 182.

An engagement groove 186 is formed in the overall periphery of a portion in the vicinity of a coupling portion between a rear end portion of the bendable portion 183 and a front end portion of a flexible tube 185. A plurality of engagement projections 187 of an insulating material project from the outer periphery of a rear end portion of the tip structure body 182.

A rib 188 detachably engaged with the engagement groove 186 inwardly projects from the inner periphery of that insertion end portion of the tip cover 184 which corresponds to the groove 186, and engagement holes 189 detachably engaged with the engagement projections 187 are formed in those portions of the tip cover 184 which correspond to the projections 187.

Moreover, a hard finger-driven portion 190 to be used to attach/detach the tip cover 184 is provided over the entire periphery of that portion of the flexible tube 185 which is located rearward of the engagement groove 186. The portion 190 is formed by applying a coating material to the outer periphery of a front end portion of the flexible tube 185 or winding a tape thereon, etc., and has a color differing from the other portions of the endoscope.

The elastic material of the tip cover 184 is fluoro rubber, silicone rubber, EPT, etc. That portion of the tip cover 184 which covers the tip structure body 182 has a relatively great thickness of about 0.7-3 mm, and that portion of the cover 184 which covers the coating member 191 of the bendable portion 183 has a relatively thin thickness of about 0.1-0.5 mm. As a result, the portion of the cover 184 in the vicinity of the tip structure body 182 is formed sufficiently strong, and the portion of the cover 184 mounted on the coating member 191 of the bendable portion 183 has high attachability/detachability. Further, the bending operation of the bendable portion 182 is not adversely affected by the tip cover 184. The ratio of the inner diameter of the tip cover 184 to the outer diameters of the coating member 191, the tip structure body 182, etc. is set to a value of 0.6-1.3.

The above-described structure has the following advantages:

Since the tip cover 184 covers the coating member 191 of the bendable portion 183, too, leakage of water due to damage in the coating member 191 can be prevented. Accordingly, an expensive photographing unit is sufficiently protected, and it is not necessary to repair or exchange the member 191.

In addition, a color differing from that of the other portions is imparted to the front end portion of the flexible tube 185 by applying a coating material thereto or winding a tape thereon, thereby forming the finger-driven portion 190. Therefore, the portion 190 can easily be discriminated from the flexible tube 185, and hence the attachment/detachment of the tip cover 184 can easily be performed at high efficiency. Further, the flexible tube 185 can have a smooth outer peripheral surface, making it easier to insert the endoscope into a body cavity.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An endoscope apparatus comprising:
    an insertion portion to be inserted into a body cavity, the insertion portion having a tip portion;
    said tip portion of the insertion portion including a tip structure;
    a tip cover detachably mounted on the tip structure from a side of a tip portion of the tip structure, the tip cover covering the tip structure;
    an engagement device provided on the insertion portion for detachably engaging the tip cover; and
    a hard finger-driven engaging/disengaging member provided on an outer periphery of a portion of the insertion portion which is located in the vicinity of the engagement device.

2. The apparatus according to claim 1, wherein the hard finger-driven engaging/disengaging member comprises a finger-driven member having an insulating portion insulated from the tip structure.

3. The apparatus according to claim 1, wherein the hard finger-driven engaging/disengaging member comprises a finger-driven portion coated with an insulating material.

4. The apparatus according to claim 1, wherein the tip cover comprises a soft elastic material.

5. The apparatus according to claim 1, wherein the tip cover includes a cylindrical cover body mounted on the tip structure from the side of the tip portion of the tip structure, and reinforcing means for reinforcing the cover body.

6. The apparatus according to claim 5, wherein the reinforcing means includes means for engaging with the engagement device.

7. The apparatus according to claim 5, wherein the reinforcing means includes a reinforcing member at least partially buried in the cover body of the tip cover.

8. The apparatus according to claim 7, wherein the tip structure includes a first engagement portion for engaging the tip cover, and the reinforcing member includes a second engagement portion for engaging the first engagement portion.

9. The apparatus according to claim 8, wherein the first engagement portion comprises a concave portion or a hole portion in the tip structure, and the second engagement portion comprises a convex portion for engaging the first engagement portion.

10. The apparatus according to claim 9, wherein the first engagement portion and the second engagement portion each have engagement members which engage each other to prevent the tip cover from easily coming off the tip structure.

11. The apparatus according to claim 1, wherein:
    the tip structure includes a substantially flat recessed portion obtained by partially cutting an outer periphery of a front portion of the tip structure, and the substantially flat recessed portion has an optical-system mounting portion in which an illuminating optical system and a photographing optical system are mounted, and a hole for receiving a forceps-raising table, the forceps-raising table adjusting an angle of projection of forceps in the insertion portion when forceps are projected to an outside of the insertion portion; and the tip cover includes an opening formed corresponding to the optical-system mounting portion and the forceps-raising table receiving hole of the tip structure, and a thick portion which comprises at least part of an edge of the opening and located near the forceps-raising table, the thick portion being thicker than other portions of the tip cover.

12. The apparatus according to claim 11, wherein:

the tip structure includes a hole for receiving the photographing optical system, and a fixing means for fixing the photographing optical system in the hole; and the fixing means is located at a portion of the tip structure which is more remote from the tip portion of the tip structure than a rear end portion of the tip cover.

13. The apparatus according to claim 1, wherein the tip cover includes an insertion end portion provided with a plurality of engagement portions for engaging the engagement device.

14. The apparatus according to claim 13, wherein the engagement device includes a plurality of engagement depressions, and the engagement portions of the tip cover include engagement projections for disengageably engaging the engagement depressions.

15. The apparatus according to claim 13, wherein:

the engagement device includes a plurality of projections projecting from the tip structure; and the engagement portions of the tip cover include engagement holes for disengageably receiving the engagement projections.

16. The apparatus according to claim 1, wherein the tip structure includes:

a circumferential engagement portion for engaging the tip cover in a circumferential direction of the tip structure; and an axial engagement portion for engaging the tip cover in an axial direction of the tip structure;

the tip cover having a first uneven surface portion for engaging the circumferential engagement portion and a second uneven surface portion for engaging the axial engagement portion.

17. The apparatus according to claim 1, wherein the tip structure includes:

a hole which receives a forceps-raising table for adjusting an angle of projection of a treatment tool in the insertion portion when the treatment tool is projected to an outside of the insertion portion; and a curved guide portion for guiding the treatment tool, the curved guide portion having a first guide portion formed integral with the tip structure as one body, and a second guide portion insulated from the first guide portion.

18. The apparatus according to claim 1, wherein the tip structure includes:

a hole which receives a forceps-raising table for adjusting an angle of projection of a treatment tool in the insertion portion when the treatment tool is projected to an outside of the insertion portion; and a raising-table shaft supporting the forceps-raising table such that the table can rotate, the raising-table shaft having slippage-preventing means for preventing the forceps-raising table from slipping.

19. The apparatus according to claim 1, wherein:

the tip structure includes a hole which receives a forceps-raising table for adjusting an angle of projection of a treatment tool in the insertion portion when the treatment tool is projected to an outside of the insertion portion; and a raising-table shaft supporting the forceps-raising table such that the table can rotate, the raising-table shaft having a first hole which receives an operation shaft arranged rotatable therein and attached to an end of an operation wire to be pushed and pulled by a proximal operating section coupled with a proximal end of the inserting portion, and a second hole which receives the raising-table shaft such that the shaft can rotate; and a cleaning liquid passage is provided on at least one of a portion of the operation shaft which is fitted in the first hole and a portion of the operation shaft which is fitted in the second hole.

20. The apparatus according to claim 19, wherein the cleaning-liquid passage comprises a cleaning-liquid passage hole.

* * * * *